United States Patent [19]

Ruhenstroth-Bauer

[11] Patent Number: 4,631,957

[45] Date of Patent: Dec. 30, 1986

[54] METHOD FOR ALERTING PATIENTS WITH DISEASES AFFECTED BY CLIMATE, SUCH AS EPILEPSY AND MYOCARDIAL INFARCTION

[75] Inventor: Gerhard Ruhenstroth-Bauer, Gräefelfing, Fed. Rep. of Germany

[73] Assignee: Atmospheric Weather Analysis Systems, Fed. Rep. of Germany

[21] Appl. No.: 576,520

[22] Filed: Feb. 2, 1984

[30] Foreign Application Priority Data

Mar. 25, 1983 [DE] Fed. Rep. of Germany ....... 3310908

[51] Int. Cl.$^4$ ........................................... G01W 1/00
[52] U.S. Cl. ................. 73/170 R; 128/1 R; 340/601
[58] Field of Search ............. 73/170 R; 340/573, 601; 324/77 E; 128/1 R

[56] References Cited

U.S. PATENT DOCUMENTS 3,753,117  8/1973  Downing et al. ................... 325/364
3,881,154  4/1975  Lewis et al. ......................... 325/67
4,095,221  6/1978  Slocum, Jr. ........................ 340/421

OTHER PUBLICATIONS

Eine Anlage zur Registrierungder Atmospherics bei 10 und 27 khz, H. Baumer and J. Eichmeier, Arch. Met. Geoph. Biokl., Ser. A, 29, 1980, pp. 143-155.
Die Atmospherics-Aktivitat bei 10 und 27 khz als Indikator fur die Dymamik der Tropospharischen Wettervorgange, W. Sonningv, H. Baumer and J. Eichmeier, Arch. Met. Geoph. Biokl., Ser. B, 29 (1980), pp. 299-312.
The Biophysically Active Waveforms of Atmospheres Incident on Gelatin; Films: H. Baumer and J. Eichmeier, Int. J. Biometeor., vol. 26, 1982.
Die Meteorotropis eines Dichromat-Gelatinesystems, Hans Baumer, Tech. Informationsdienst des Bundesverhand Druck e. V. II/1982.

Primary Examiner—John F. Niebling
Assistant Examiner—William T. Leader
Attorney, Agent, or Firm—Jones, Tullar & Cooper

[57] ABSTRACT

A method for alerting patients with diseases affected by climate, such as epilepsy and myocordial infarction, according to which sinusoidal spheric pulses having a frequency of 28 kHz and sinusoidal spheric pulses having a frequency of 10 kHz are measured by a spheric selector circuit. The pulse rate of these spheric pulses is ascertained over a predetermined period of time and the difference between the pulse rates of the spheric pulses at 28 kHz and those at 10 kHz is ascertained. If the spheric pulses having a frequency of 28 kHz predominate, then the patient is alerted by means of a signal generated by a circuit which includes the spheric selector circuit for carrying out the method.

2 Claims, 6 Drawing Figures

METHOD FOR ALERTING PATIENTS WITH DISEASES AFFECTED BY CLIMATE, SUCH AS EPILEPSY AND MYOCARDIAL INFARCTION

BACKGROUND OF THE INVENTION

The invention relates to a method for alerting patients with diseases affected by climate, such as epilepsy and myocardial infarction, and a circuit layout for performing the method.

From very early times, the weather has been felt to be a very important factor in the occurrence of certain diseases. Among these are, in particular, epilepsy and myocardial infarction. Many attempts have already been made to correlate the so-called classical parameters of weather, such as the absolute or relative humidity, the average temperature, particular phases of weather, and so forth with the frequency of occurrence of these diseases, in particular, in order, if possible, to be able to take particular prophylactic measures. Thus far all that has been accomplished is to make measurements offering little in the way of information.

OBJECT AND SUMMARY OF THE INVENTION

It is an object of the present invention to provide a method which makes it possible to predict climatically unfavorable or favorable conditions for diseases affected by climate, especially episodic diseases such as epilepsy and myocardial infarction. A circuit layout for alerting the patient is also to be provided.

In accordance with the invention this object is obtained by means of a method characterized in that the sinusoidal spheric pulses having a frequency of 28 kHz and the sinusoidal spheric pulses having a frequency of 10 kHz are measured by a spheric selector having appropriate antennas, amplifier, and filters. The pulse rate of these spheric pulses is then ascertained over a predetermined period of time, and the difference between the pulse rates of the spheric pulses at 28 kHz and those at 10 kHz is ascertained; finally, if these spheric pulses having a frequency of 28 kHz predominate, then communication devices for alerting patients are actuated.

The invention is thus based on the recognition that for the climatic influences on these diseases it is not the weather itself that is responsible, but rather particular electromagnetic oscillation phenomena occurring in weather formation, namely so-called "spheric pulses", or spherics, of particular frequency and in particular combination. The spheric pulses are a damped oscillation with from 5-10 half waves and a substantially exact sinusoidal shape, which are apparently formed during discharge events in the atmosphere (a spheric pulse is shown in FIG. 3 in the first line, left-hand column). The shape of such spheric pulses is known; see J. Eichmeier, "Eine Anlage zur Registrierung der Atmospherics bei 10 und 27 kHz" ("A System for Recording Atmospherics at 10 and 27 kHz") Arch. Meteor. Geophysik, Bioklimat., A, 29: 143–155 (1980); and W. Sönning, H. Baumer, and J. Eichmeier, "Die Atmospherics-Aktivität bei 10 and 27 kHz als Indikator für die Dynamik der troposphärischen Wettervorgänge", ("The Activity of Atmospherics at 20 and 27 kHz as an Indicator for the Dynamics of Tropospheric Weather Processes"), Arch. Meteor. Geophysik, Bioklimat., B, 29: 299–312 (1981).

Although the analysis of the weather dependency of a dichromate-gelatine system used at low pressure has already shown the biological effect of particular spheric pulses, the invention is not thereby rendered obvious (see Baumer, "Die Meteorotropie eines Dichromat-Gelatinesystems" ["Meteorotropy of a Dichromate-Gelatine System"], Techn. Informationsdienst des Bundesverbands Druck e.V. II/1982). The correlation between the appearance of these spheric pulses, that is the indicated combination thereof, with the indicated clinical pictures, which are demonstrated below particularly epilepsy and myocardial infarction furthermore results in the further inventive recognition that in this manner endangered patients can be forewarned.

Exemplary embodiments of the invention will be described below, referring to the drawings.

DESCRIPTION OF THE PREFERRED EMBODIMENTS

The spheric pulses at 28 kHz (to be exact: 28018.17 Hz) are received with the aid of four horizontally disposed ferrite antennas 1–4. The four ferrite antennas are horizontally aligned in the four directions, north, south, east, and west. The horizontal disposition is in accordance with the fact that these spheric pulses are electromagnetic waves having a horizontally polarized magnetic field component. A vertically disposed wide-band antenna 5 is also provided. It serves to receive the spheric pulses having a vertically polarized electrical field component and to divert spheric pulses having frequencies between 3 and 100 kHz. Measurements have shown that in this range spectral maximums of spheric pulses exist. These are marked a, b, c, and d. In the present context, the spheric pulses having a frequency of 10.38 kHz (simplified herein to 10 kHz) are of particular significance.

The antennas 1–4 are connected with the spheric selectors 10–13 via preamplifiers 6–9. Both the antennas 1–4 and the spheric selectors 10–13 for the spheric pulses at 28 kHz are marked in accordance with the directions from which these antennas receive the spheric pulses, being marked $28_I$, $28_{II}$, $28_{III}$, and $28_{IV}$.

The wide-band antenna 5 is connected via the preamplifier 14 with the spheric selectors 15–20 for these frequencies.

For regulating the reception range, the regulation means of the preamplifiers 6–9 and 14 is used, which receives a control signal emitted by a control transmitter at an always-constant transmitting amplitude and controls these preamplifiers depending upon the level of this reception, so that differences in damping in the transmission path from the location where the spheric pulses arise to the location where the antennas 1–5 are disposed are compensated for. The adjustment is accomplished via the control circuit 22.

Each of the spheric selectors 10–13, 15–20 is provided with two outputs. The upper outputs A lead to recorders, not shown in detail; the lower outputs B lead to inputs of the circuit according to FIG. 5.

Figure 1:
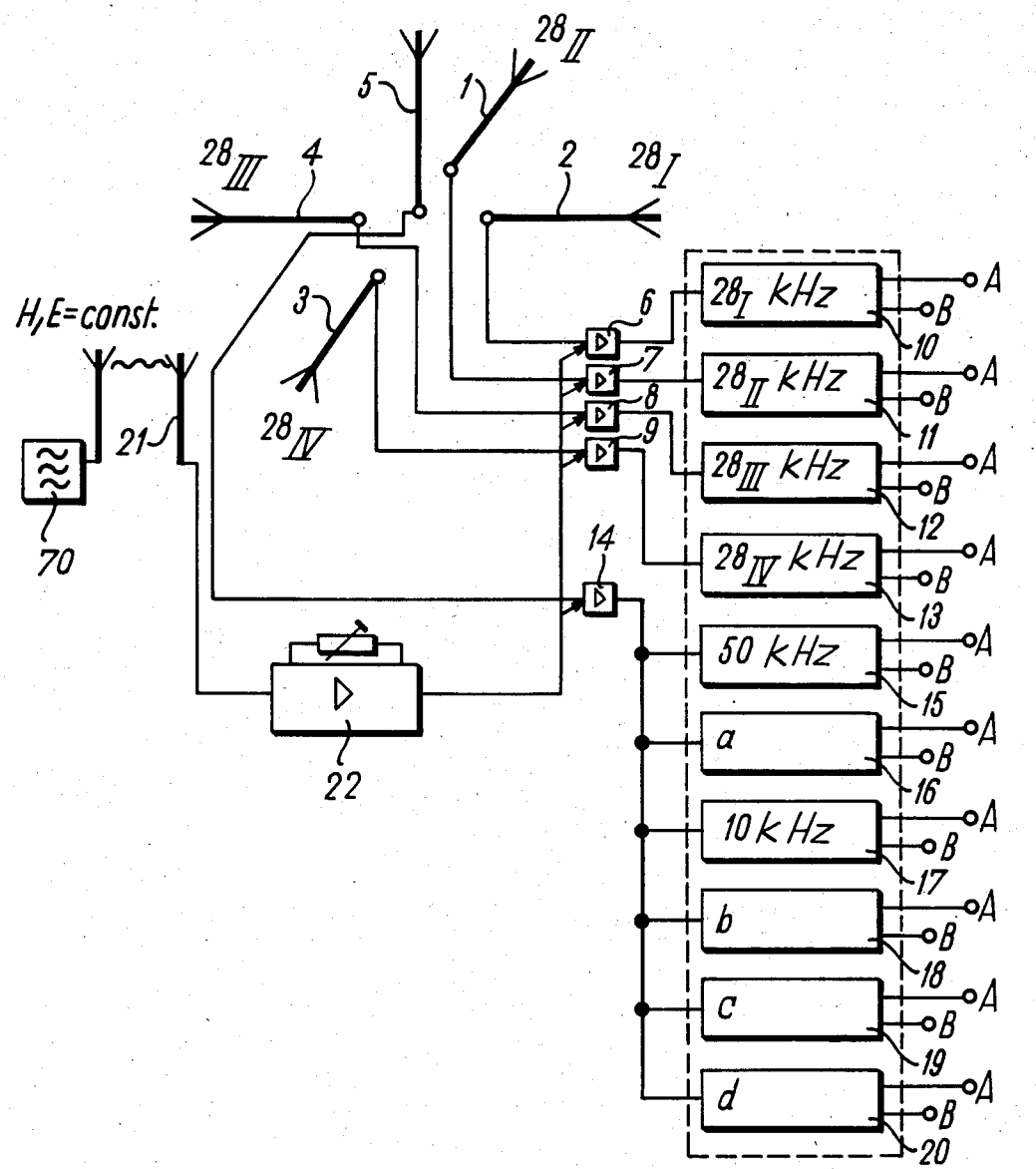
FIG. 1 shows the input part of a circuit layout according to the invention.
Figure 2:
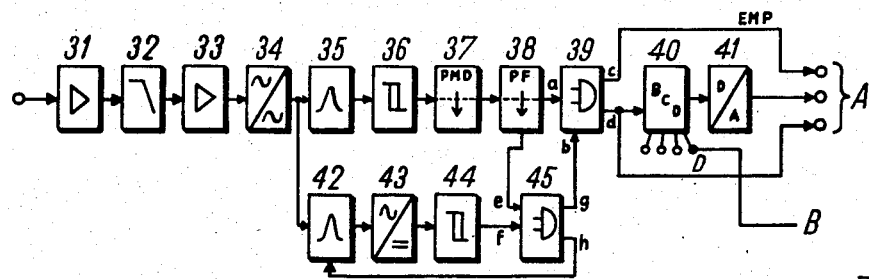
FIG. 2 is a detailed view of the spheric selectors used in FIG. 1.

The spheric selectors 10–13 have the design shown in FIG. 2. This design serves to identify a spheric pulse, such as is shown in the left-hand side of the first line in FIG. 3, and simultaneously to filter out pulses of the type shown on the right-hand side of the first line in FIG. 3, which are so-called EMP pulses.

The "electromagnetic pulse" (EMP) is a "primal pulse" arising at very short range, which is biologically ineffective and must be filtered out in making the measurement. It can be called a primal pulse because in this form all the frequencies up to and on into the MHz range are present, and there is some support for the hypothesis that from this primal pulse, by means of filtering, the biologically effective spheric pulses arise in air masses characterized by particular meteorotrophic properties.

The spheric selector 10 is embodied by an input amplifier 31, a low-pass filter 32, a further amplifier 33 which is matched to the special frequency of the particular spheric selector, a limiter 34, a band-pass filter 35, a Schmitt trigger 36, a pulse-missing detector 37, a pulse shaper 38, a logic network 39, and a decimal counter 40. At the output of the limiter 34, other elements are connected parallel to these circuit units listed above, specifically: a further band-pass filter 42 having a restricted band-pass range, a full-wave rectifier 43, a further Schmitt trigger 44, and a second logic network 45. The inputs of the logic network 39 are marked a and b, and those of the second logic network 45 are marked e and f; the outputs of the logic network 39 are marked c and d, and the outputs of the logic network 45 are marked g and h.

Figure 3:
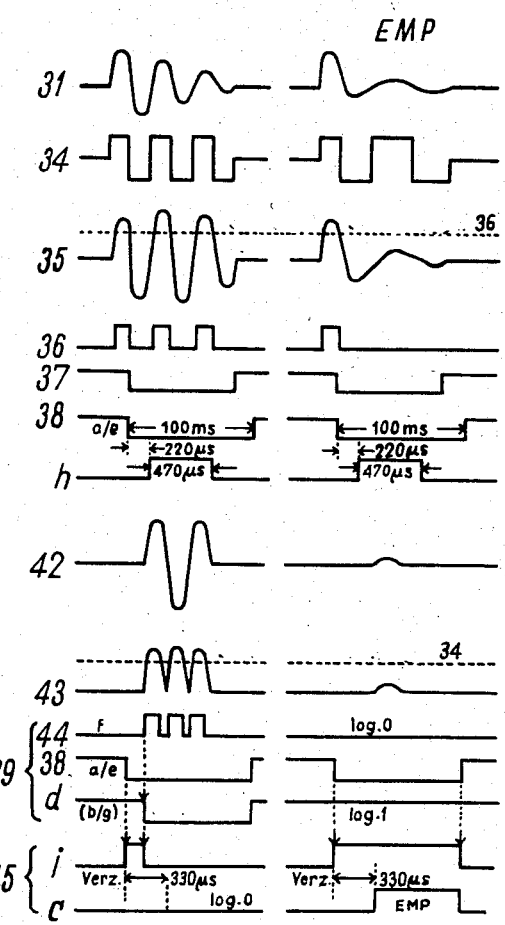
FIG. 3 shows various pulse shapes at various locations in the circuitry of FIG. 2.

The outputs of these circuit units are shown in part in FIG. 3 in the lines thus labeled, specifically in the left-hand column for the case of a spheric pulse at the input and in the right-hand column for the case of an EMP at the input. The circuit causes a signal to appear at output d of the logic network 39 in the case of the spheric pulse, but not in the case of an EMP pulse. Upon the appearance of an EMP pulse, no pulse appears at the output d of the logic network 39. The EMP pulse can be picked up at output c. The functioning can be described in detail as follows:

The signal amplified in the amplifiers 31 and 33 and from which higher-frequency components have been removed in the low-pass filter 32 is brought in the limiter 34 to a uniform amplitude. The band-pass range is fixed (for instance at from 20–30 kHz) by means of the band-pass filter 35 and the Schmitt trigger 36. At the same time, the signal is given a rectangular shape (see the corresponding curved shapes at the output of the Schmitt trigger 36 in FIG. 3). The pulse-missing detector 37 is in principle a retriggerable monostable multivibrator (hereinafter, monovibrator), that is, a circuit unit which is switched over by a negative flank of a pulse and after a predetermined adjustable period of time returns to its initial status, as long as a new pulse is not present. In other words, the pulse-missing detector 37 is switched over from "1" to "0" by the lagging flank of the first half-wave of the spheric pulse. However, it does not return to "1", where it can thus admit a further signal for further pulse shaping to the pulse shaper 38 connected to its output side, unless for a predetermined period of time, within which it must have returned to "1", no further half-wave is present. In this manner, man-made persistent oscillations, such as are generated for instance by electrical appliances in the vicinity of the antennas (so-called man-made oscillations) are filtered out. In the pulse shaper 38, a pulse of up to 100 ms long is formed. This pulse is also sent to the logic network 45, and from the logic network 45, after a predetermined, preestablished delay, provides at the output h a gating pulse which opens the switching path via the circuit units 42, 43 and 44. The spheric pulse can thus be distinguished from the EMP pulse.

In the case of the spheric pulse, the first half-wave is followed by a still further half-wave having an amplitude which is smaller than that of the first half-wave yet is still high enough to switch the following Schmitt trigger 34; this is not the case with an EMP pulse. A signal thus arises at the output f only when a sinusoidal spheric pulse has been present at the input. Thus if signals are present both on the line a at the output of the pulse shaper 38 (monovibrator having a pulse width of up to 100 ms), and on the line g at the output of the second largest network 45 simultaneously, that is, if a spheric pulse has been present at the input, then at output d of the first logic network 39 a pulse appears; on this point, see the third-from-last line in the left-hand column in FIG. 3. At the output D of the decimal counter 40, a reduction of the pulse rate by 1:10 occurs.

Figure 4:
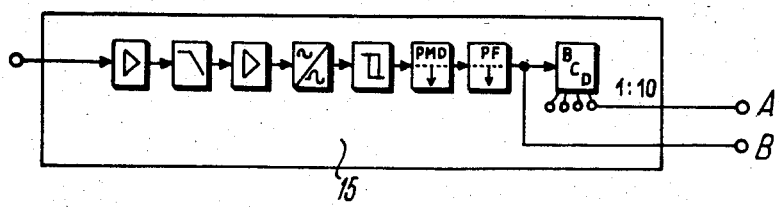
FIG. 4 is a detailed view of a further spheric selector among those used in FIG. 1.

FIG. 4 shows the spheric selector 15, as an example of one of the spheric selectors 15–20. It is identical in design to the spheric selector of FIG. 2 in principle, but with the distinction that the circuit units 42–45 are not provided. In the case of these frequencies these units can be dispensed with, because they relate to vertically polarized magnetic fields which do not have any EMP component that needs to be filtered out.

The two outputs of each of the spheric selectors are marked A and B. The outputs A reach a recorder, not shown in further detail, while the outputs B reach the output processor shown in FIG. 5. The channels are marked with the corresponding frequencies. The pulse train frequencies are emitted, for instance, in a scanning cycle of 8 minutes at a pulse rate of from 0 to 320 Hz (class 1), 320 to 2560 Hz (class 2) and at more than 2560 Hz (class 3).

Figure 5:
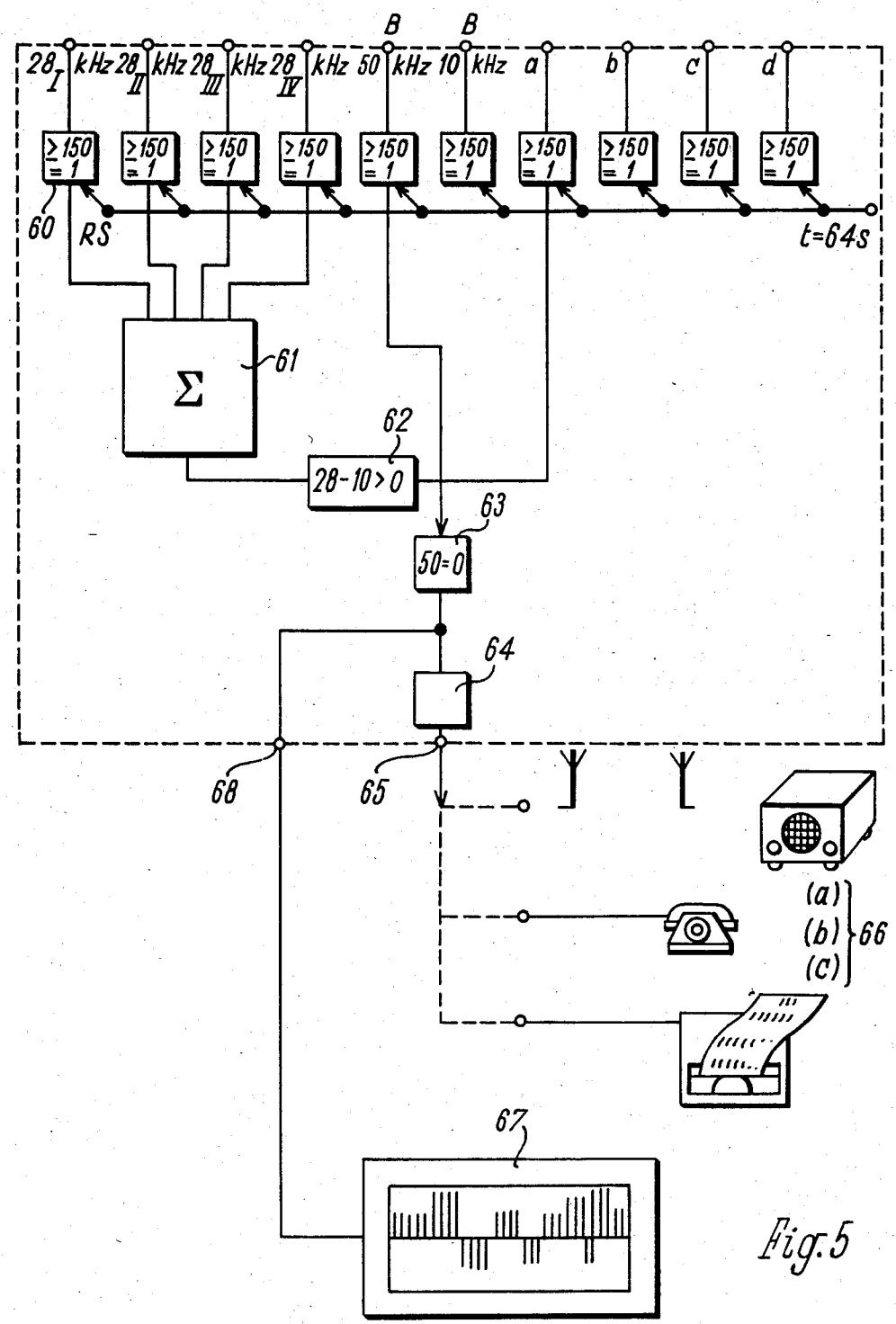
FIG. 5 is an output processor such as is used in connection with the circuitry used in FIG. 1.

The output processor which is critical for alerting patients with diseases affected by climate in accordance with the invention is shown in FIG. 5. The input B of the corresponding channels first travel to counters 60, which emit an output signal for each 150 signals at the input and are reset again after each 64 seconds (64s). If within the cycling time of 64s an output signal has appeared at a counter 60, then the frequency of the spheric pulses ascertained in the preceding spheric selector was greater than 150/64, or in other words, greater than approximately 2.5 Hz. The output signals of the counters 60 of the channels $28_I$, $28_{II}$, $28_{III}$, $28_{IV}$ kHz are added up in the summing circuit 61. In the subtracting network 62, the number of pulses at 10 kHz occurring within the timing cycle is subtracted from this sum, and the difference, if it is not equal to zero is emitted at the output of the subtracting network 62. From there, it reaches a network 63, which emits a pulse only if spheric pulses in the range of 50 kHz are not also measured at the same time. This is because spheric pulses of this frequency are possibly to be considered as interference which reduces the biological effect of the spheric pulses at 28 kHz and 10 kHz. Reference numeral 64 indicates a coder which translates the output signals of the network 63 into a form suited to the following communication devices 66. Three examples of suitable communication devices are shown, namely first a radio transmission means, marked (A), telephone transmission, marked (B), and telex transmission, marked (C). A fourth possibility would be reception by means of a particular community TV antenna to which a subscriber is connected via cable.

The transmission of an alert by one of the courses shown thus takes place in the following cases:

At a frequency of more than 1.0 Hz, spheric pulses occur in the channels associated with a frequency band of 28 kHz; these are pulses such as are shown in the left-hand column of FIG. 3 in the first line.

The frequency of the spheric pulses at more than 1.0 Hz is greater than those at 10 kHz.

Spheric pulses do not simultaneously occur in the frequency band of 50 kHz; by means of the appropriate circuit, So-called EMP pulses of the type shown in the first line, right-hand column in FIG. 3 are filtered out; and furthermore, Man-made persistent oscillations are filtered out.

It has now been found that the signals as they are derived in this manner and are available at the output 65 of the output processor shown in FIG. 5 do correlate with certain climatically affected diseases, with epilepsy and myocardial infarction being explained below as examples of such diseases. Thus the circuitry shown does represent a suitable alerting device for patients who suffer from these diseases. Upon the appearance of an alert of this kind, the patients can take prophylactic medications or avoid particular risk situations.

It should additionally be noted with respect to the circuitry shown in FIGS. 1-5 that the channels shown for the frequencies between 3 and 100 kHz have been included in the drawings because spheric pulses also occur at these frequencies, as has been mentioned. However, the question of whether they have a biological effect, and if so to what extent, has not yet been answered completely.

In the output processor shown in FIG. 5 an output 68 is also shown, by way of which a recorder 67 records the difference between the pulse rate of the 28 kHz spheric pulses and the pulse rate of the 10 kHz spheric pulses.

Figure 6:
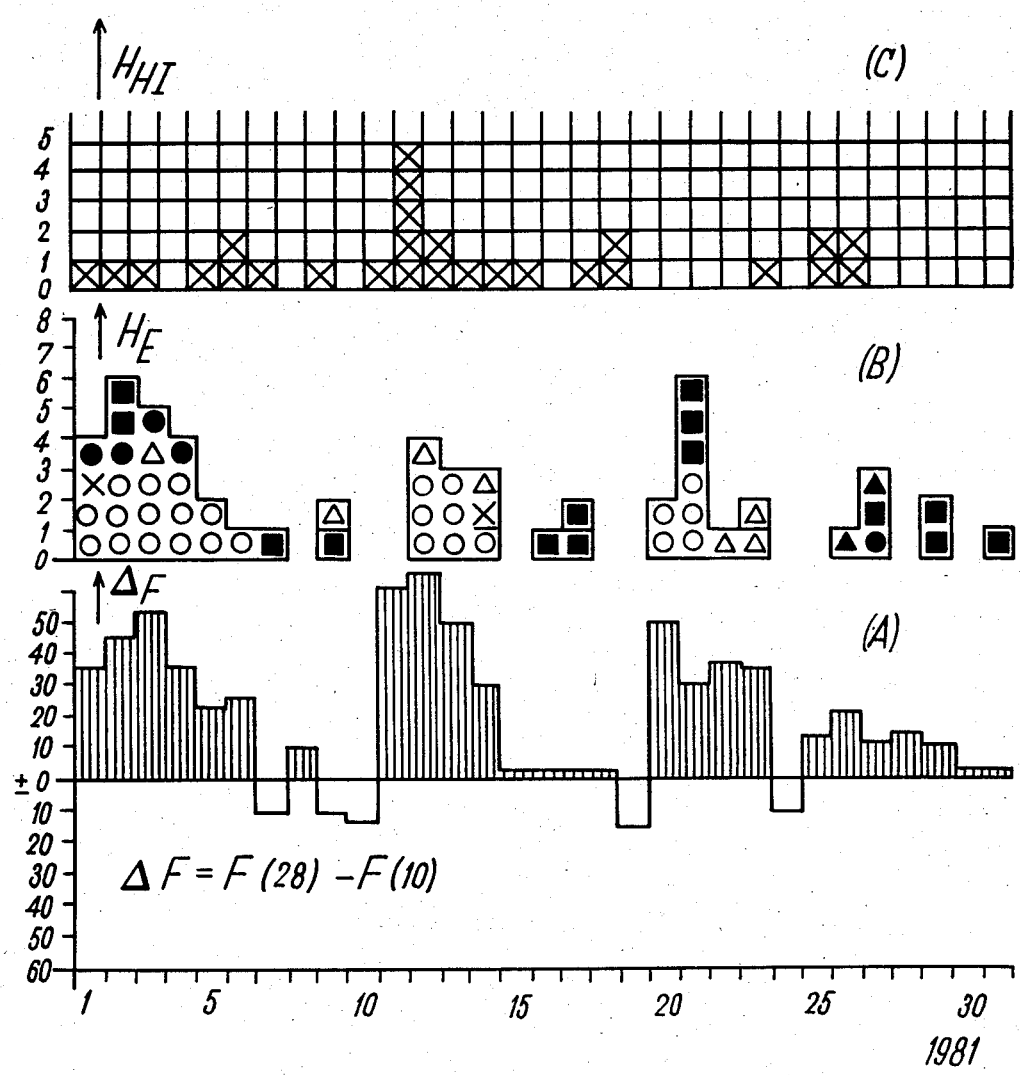
FIG. 6 is a diagram showing the correlation of the occurrence of particular combinations of spheric pulses with the frequency of episodes of epilepsy or the frequency of myocardial infarctions in particular groups of test subjects.

FIG. 6, in curve (A), shows the result of a recording of this time for the period of January 1981. As long as the curve is above the zero line, this means that the spheric pulses at 28 kHz have predominated; if the curve extends below the zero line, then the spheric pulses at 10 kHz predominated.

Correspondingly, the frequency $H_E$ of epilepsy episodes of six patients were plotted in curve (B) (the various symbols in (B) designate the various patients). The curve (C) shows the frequency during this same period of myocardial infarction in a total of four hospitals in Munich.

The graph shown in FIG. 6 already demonstrates a high correlation between a high value of the difference between the pulse rates of spheric pulses at 28 kHz and those at 10 kHz and the frequency of epileptic episodes and myocardial infarctions. The following information should also be noted in this respect:

For the six test subjects for which the frequency of epileptic episodes was studied in the period of time under observation and the frequency of the occurrence of spheric pulses was correlated in the manner illustrated, the following Spearman rank correlation coefficients (as defined, for instance, in Hartung, Elpelt, and Klösener, Statistik [Statistics], R. Oldenbourg Verlag, Munich and Vienna, 1982, page 79):

| SPEARMAN RANK CORRELATION COEFFICIENTS | | | |
|---|---|---|---|
| Test Subject | Number of Episodes | Spheric pulse at 28 kHz | Spheric pulse at 10 kHz |
| A | 94 | 0.18 | −0.13 |
| B | 10 | 0.11 | −0.11 |
| C | 62 | 0.10 | 0.06 |
| D | 31 | 0.28 | −0.15 |
| E | 71 | 0.20 | −0.24 |
| F | 47 | −0.07 | 0.03 |

From the positive correlation with the 28 kHz spheric pulses and the negative correlation with the 10 kHz, it can be concluded that the difference between the two clearly represents the deciding condition. The numbers given in the above table relate not only to a single month, however, as in FIG. 6, but rather to a period of seven months under observation. The fact that the correlations differ among the individual test subjects is an indication of the observation that in the case of epilepsy there are subgroups which are apparently affected differently by climatic conditions.

In order to further study the correlation of a positive value for the difference of the 28 kHz spheric pulses and the 10 kHz spheric pulses with the occurrence of myocardial infarction, the total myocardial infarction calendar of four Munich hospitals was evaluated for the period from Jan. 1, 1981 through July 31, 1981. The following Spearman rank correlation coefficients were determined (the probability of error is given in parentheses):

| | | |
|---|---|---|
| 10 kHz Spheric pulse | −0.10 | (0.15) |
| 28 kHz Spheric pulse | 0.13 | (0.065) |
| Absolute humidity | −0.17 | (0.015) |
| Average temperature | −0.13 | (0.056) |
| Maximum temperature | −0.12 | (0.072) |
| Minimum temperature | −0.15 | (0.028) |
| Weather phase | 0.02 | (0.78) |
| Weather event | −0.05 | (0.47) |

In this table, in addition to the spheric pulses under consideration, other parameters of weather are also listed, namely the absolute humidity, the average temperature, the highest temperature, the lowest temperature, the weather phase (that is the transition from bad weather to good weather or vice versa) and the weather event (for instance, rain). The table shows that the usual parameters of weather, which it would be considered obvious to observe first in studying weather sensitivity, do not correlate positively with the occurrence of myocardial infarction, while the 28 kHz spheric pulses discovered in accordance with the invention do so correlate.

What is claimed is:

1. A method for alerting patients with diseases affected by climate, such as epilepsy and myocardial infarction, to conditions conducive to attacks, comprising the steps of:

measuring the sinusoidal spheric pulses of a frequency of 28 kHz and 10 kHz;

ascertaining the pulse rate of said spheric pulses over a predetermined period of time;

determining the difference between the pulse rate of the spheric pulses at 28 kHz and those at 10 kHz; and alerting a patient when the spheric pulses at a frequency of 28 kHz predominate over those at 10 kHz.

2. The method as defined in claim 1, wherein only pulse rates greater than 1.0 Hz are ascertained.

* * * * *